US012338191B2

(12) United States Patent
Slezack-Deschaumes et al.

(10) Patent No.: US 12,338,191 B2
(45) Date of Patent: Jun. 24, 2025

(54) BIOFERTILIZING BACTERIAL STRAIN

(71) Applicants: Université de Lorraine, Nancy (FR); Institut National de la Recherche Agronomique, Paris (FR)

(72) Inventors: Sophie Slezack-Deschaumes, Commercy (FR); Séverine Piutti, Barisey au Plain (FR); Pierre L'Yvonnet, Perreux (FR); Sandro Roselli, Commercy (FR)

(73) Assignees: Universite de Lorraine, Nancy (FR); Institut National de la Recherche Agronomique, Paris (FR)

( * ) Notice: Subject to any disclaimer, the term of this patent is extended or adjusted under 35 U.S.C. 154(b) by 1039 days.

(21) Appl. No.: 17/415,204

(22) PCT Filed: Dec. 19, 2019

(86) PCT No.: PCT/FR2019/053222
§ 371 (c)(1),
(2) Date: Jun. 17, 2021

(87) PCT Pub. No.: WO2020/128375
PCT Pub. Date: Jun. 25, 2020

(65) Prior Publication Data
US 2022/0055960 A1    Feb. 24, 2022

(30) Foreign Application Priority Data
Dec. 20, 2018 (FR) ...................................... 1873624

(51) Int. Cl.
*C05F 11/08* (2006.01)
*C12N 1/20* (2006.01)
*C12R 1/01* (2006.01)

(52) U.S. Cl.
CPC .............. *C05F 11/08* (2013.01); *C12N 1/205* (2021.05); *C12R 2001/01* (2021.05)

(58) Field of Classification Search
CPC ...... C05F 11/08; C12N 1/205; C12R 2001/01
See application file for complete search history.

(56) References Cited

PUBLICATIONS

International Search Report issued in corresponding International Patent Application No. PCT/FR2019/053222 dated Mar. 20, 2020.
Madhaiyan et al., "*Microbacterium azadirachtae* sp. nov., a plant-growth-promoting actinobacterium isolated from the rhizoplane of neem seedlings," International Journal of Systematic and Evolutionary Microbiology, 60: 1687-1692 (2010).
Database WPI [online] XP002794053, Thomson Scientific, vol. 2018, No. 39, AN 2018-30921R (2018).
Ji et al., "Isolation and characterization of plant growth promoting endophytic diazotrophic bacteria from Korean rice cultivars," Microbiological Research, 169: 83-98 (2014).
Zinniel et al., "Isolation and Characterization of Endophytic Colonizing Bacteria from Agronomic Crops and Prairie Plants," Applied and Environmental Microbiology, 68 (5): 2198-2208 (2002).

*Primary Examiner* — Robert A Wax
*Assistant Examiner* — John W Lippert, III
(74) *Attorney, Agent, or Firm* — Morgan, Lewis & Bockius LLP

(57) ABSTRACT

The present invention relates to the field of crop fertilization, and particularly to a biofertilizing bacterial strain. In particular, the present invention relates to the bacterial strain deposited on Oct. 24, 2018, at the Collection Nationale de Culture de Microorganismes (CNCM), 28 rue du Dr. Roux, 75724 PARIS CEDEX 15, under the Budapest Treaty under number CNCM I-5373, and to the uses of this strain. The invention also relates to a composition comprising the above-mentioned bacterial strain and to a fertilization process comprising the application of this composition to a plant or to a soil.

9 Claims, 1 Drawing Sheet
Specification includes a Sequence Listing.

[Fig. 1]
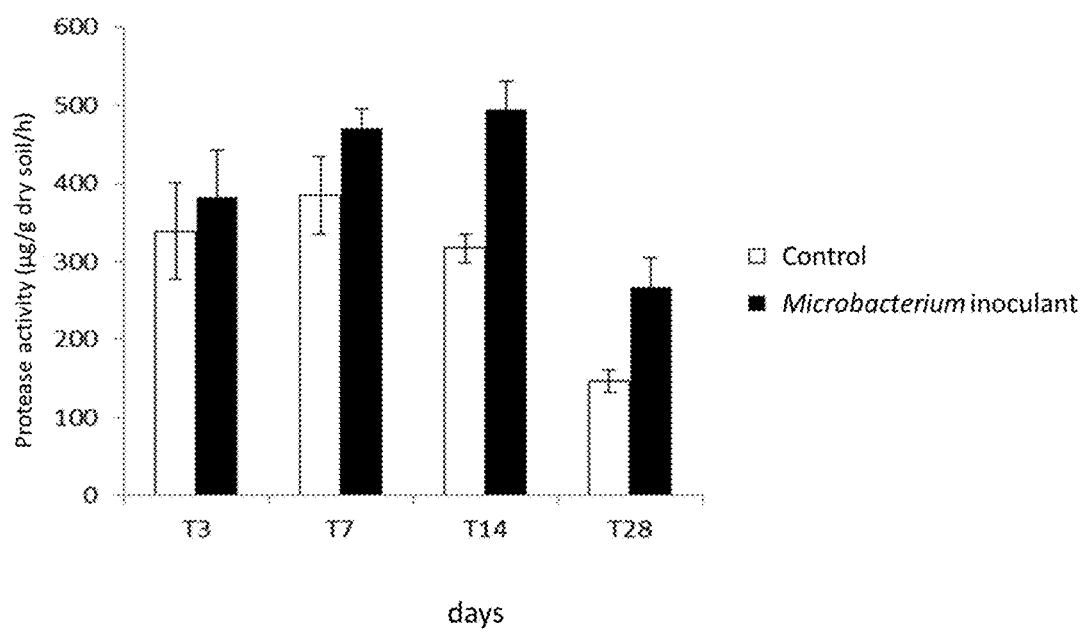
[Fig. 2]
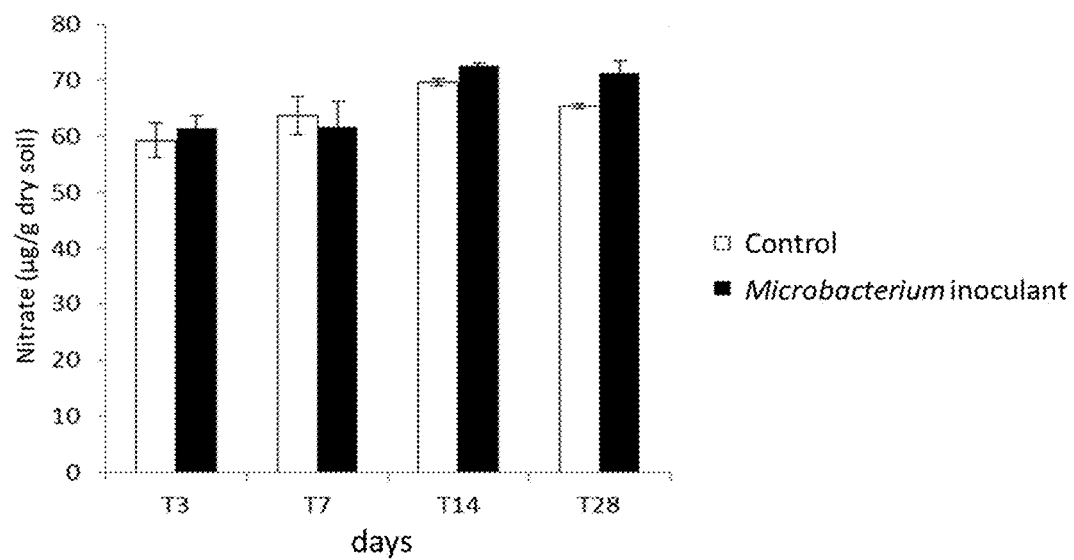

BIOFERTILIZING BACTERIAL STRAIN

SEQUENCE LISTING SUBMISSION VIA EFS-WEB

A computer readable text file, entitled "SequenceListing.txt" created on or about Jun. 17, 2021 with a file size of about 1 kb contains the sequence listing for this application and is hereby incorporated by reference in its entirety.

TECHNICAL FIELD

The present invention relates to the field of crop fertilization, and particularly to a biofertilizing bacterial strain.

PRIOR ART

The second half of the 20th century saw a significant intensification of agriculture in developed countries. This intensification was largely based on the use of a set of inputs which allowed better control of the factors limiting agricultural production (Tilman et al., 2002). The widespread use of chemical fertilizers provides much of the explanation for the very rapid growth of agricultural production from the 1950s onwards. However, the intensive use of mineral nitrogen (N) fertilizers has led to the transfer of these elements to surface and groundwater and the emission of greenhouse gases that contribute to the destruction of the ozone layer (Binbradan et al., 2015; Sebilo et al., 2013). In addition, N fertilizers have contributed to altering biological diversity in agrosystems, with consequences for ecosystem functioning (Tilman et al., 1997) and primary productivity (Hector et al., 1999). These socially-unacceptable negative effects result mainly from poor N fertilizer use efficiency by crops. For example, 20-80% of these fertilizers are said to be dispersed in the environment rather than being absorbed and assimilated by crops (Bindraban et al., 2015). Today, it is therefore necessary to limit the use of chemical N fertilizers.

For an element such as sulfur(S), the problem is different. Indeed, the implementation since the 1980s of international directives to reduce industrial atmospheric emissions and the reduction of the free S content of N, P and K fertilizers has paradoxically led to the appearance of S deficiencies in crops. These deficiencies can be detrimental to crop yields and quality. It is therefore necessary to improve the supply of S for crops, especially since S improves the assimilation of N in plants.

There is therefore a genuine need for non-chemical solutions, based on biological processes, that improve the availability of soil nutrients (mineral elements) to the plant (biofertilizer solution) and increase the efficiency of their use by the plant (phytostimulant solution). This is particularly important for N and S insofar as more than 90% of N and S in soils are in organic forms that must be transformed by soil microorganisms (process of decomposition and mineralization of organic matter) to release mineral forms accessible to plants.

SUMMARY OF THE INVENTION

The present invention relates to a biofertilizing bacterial strain for meeting the above needs.

Thus, in a first aspect, the present invention relates to a bacterial strain as deposited on Oct. 24, 2018, at the Collection Nationale de Culture de Microorganismes (CNCM), 28 rue du Dr. Roux, 75724 PARIS CEDEX 15, under the Budapest Treaty under number CNCM I-5373.

According to another aspect, the present invention relates to a composition comprising the bacterial strain as deposited on Oct. 24, 2018, at the Collection Nationale de Culture de Microorganismes (CNCM), 28 rue du Dr. Roux, 75724 PARIS CEDEX 15, under the Budapest Treaty under number CNCM I-5373.

The invention also relates to a fertilization process, said process comprising a step in which the composition in accordance with the invention is applied to a plant or to a growing medium such as soil.

In another embodiment, the present invention also relates to the use of the above-mentioned bacterial strain as biofertilizer or phytostimulant.

DISCLOSURE OF THE INVENTION

The present inventors have succeeded in identifying and isolating a biostimulant bacterial strain that exhibits remarkable biofertilizer properties and solves the above problems.

"Biostimulants" are defined as products containing one or more substance(s) and/or microorganisms whose function consists, when applied to plants or in the rhizosphere, in stimulating natural processes for the benefit of nutrient uptake and/or increased efficiency of nutrient use, as well as tolerance to abiotic stress factors, independently of the nutrient content of the products (Du Jardin, 2012). Depending on the biological processes influenced by the biostimulant, it can be described as a "phytostimulant," "biofertilizer," "soil life activator," or "phytoactivator" (Faessel and Tostivint, 2016).

Biostimulants therefore include solutions based on microorganisms (microbial inoculants) or organic substances of various chemical natures (Calvo et al., 2014).

Microbial inoculants include free microorganisms (bacteria and fungi) and/or symbiotic microorganisms (bacteria belonging to the Rhizobiaceae, mycorrhizal fungi). Some free bacteria that can be used as microbial inoculants, can be described as plant growth-promoting rhizobacteria (PGPR) (Hayat et al., 2010).

Microbial inoculants, including PGPR, can enhance plant growth by increasing the availability of specific mineral elements in the soil, namely phosphorus (P), potassium (K), iron (Fe), calcium (Ca), and magnesium (Mg) (Calvo et al., 2014). Microorganisms act by i) solubilizing elements such as P via the production of organic acids, ii) mineralizing organic P in the soil via phosphatase production, iii) producing siderophores.

A "biofertilizer" bacterial strain has the capacity to stimulate the biological functioning of the soil in relation to the mineralization of organic matter and to improve the availability of mineral elements, in particular N, S and even P. This capacity can result from the production of microbial enzymes for the decomposition and mineralization of elements, such as for example an arylsulfatase activity which releases mineral S or protease/aminopeptidase activities which release N.

A bacterial strain with the capacity to modify the microbial balance in soils and to improve the mineralization of organic matter globally is described as a "soil life activator".

A bacterial strain is also called "phytostimulant" when it has the capacity to stimulate the growth, in particular the root system, of plants in their early stages of development. This type of strain therefore improves soil exploration and element interception capacities by the plant. Phytostimulant strains can influence plant root development via the production of phytohormone analogues that regulate root initiation and elongation and the production of absorptive hairs (Vacheron et al., 2013).

The bacterial strain in accordance with the present invention has very strong biofertilizer, phytostimulant and soil life activators activities. Indeed, the present inventors have demonstrated in particular that the inoculation of the bacterial strain in accordance with the invention significantly increased the enzymatic activities of the soil involved in the decomposition and mineralization of N and S (and particularly the protease and arylsulfatase activities).

The inventors have also demonstrated that the strain according to the present invention significantly increases the root biomass, thus potentiating a better capture of soil minerals by the plant The bacterial strain in accordance with the invention is the strain deposited on Oct. 24, 2018, at the Collection Nationale de Culture de Microorganismes (CNCM), 28 rue du Dr. Roux, 75724 PARIS CEDEX 15, under the Budapest Treaty under number CNCM-I-5373.

After analysis (partial sequence of the 16S rDNA with a length of 1374 bp amplified with Taq PrimeStar Max), it turns out that the present strain is affiliated with the genus "*Microbacterium*" and has particularly 98% identity with *Microbacterium resistens* strain DMMZ 1710 (GenBank accession no.: NR 026437.1). In the context of the present application the bacterial strain constituting the subject matter of the invention may therefore also be referred to as a "M" or "*Microbacterium*-affiliated" strain.

The bacterial strain in accordance with the present invention may be formulated as a composition. Thus, in another aspect, the present invention relates to a composition or "inoculant", comprising the bacterial strain in accordance with the present invention. The composition may be in powder, granule, cream (or "mud") or liquid form (Bashan et al., Inoculants of plant growth-promoting bacteria for use in agriculture; *Biotechnol Adv* 16:729-770, 1998; Catroux et al, Trends in rhizobial inoculant production and use, *Plant Soil* 230:21-30, 2001). In a preferred embodiment, the bacterial strain in accordance with the invention is formulated in liquid form.

The person skilled in the art knows several ways to formulate biofertilizer bacterial compositions, or "inoculants" (see for example Bashan, Yoav, et al. "Advances in plant growth-promoting bacterial inoculant technology: formulations and practical perspectives (1998-2013)." *Plant and Soil* 378.1-2 (2014): 1-33).

In order to prepare such a composition, the bacterial strain will typically be incorporated into a carrier material. The carrier must allow the growth of the bacteria in accordance with the invention, maintain a satisfactory level of viable bacteria for a given period of time, and allow the release of these bacteria in sufficient amounts to allow their biostimulant effect (see Date et al., "Advances in inoculant technology: a brief review", *Aust J Exp Agr* 41:321-325, 2001). This carrier can be in solid, liquid or gel form. Carriers can be divided into five main categories:
- soils including peat, charcoal, biochar, clays, and inorganic soils;
- organic plant and animal wastes of industrial or agricultural origin;
- inert materials such as polymers (like alginate or chitosan) or rock fragments (like vermiculite and perlite);
- freeze-dried or dehydrated microbial cultures incorporated into a solid carrier or used as such; and
- liquid carriers that comprise the bacterial strain to be formulated alone or in the presence of certain additives to improve stability, dispersion or turbidity.

The carrier may be pre-sterilized and enriched with nutrients such as sucrose, maltose, trehalose, molasses, glucose and glycerol. This increases the viability and shelf life of the composition comprising the bacteria in accordance with the invention.

"Soil" carriers may include additives. These additives are typically selected from chitin, pyrophyllite, coal, sedimentary rocks such as lignite, sugars (monosaccharides, oligosaccharides and polysaccharides), gum arabic and mineral and organic oils.

Additives used for liquid carriers are typically selected from carboxymethyl cellulose, glycerol, sugars (monosaccharides such as glucose, galactose, fructose;

oligosaccharides and polysaccharides such as sucrose, lactose, maltose or trehalose), glycerol, ferric EDTA, gum arabic and mineral and organic oils.

The composition may contain only the bacteria in accordance with the invention, in which case it is referred to as a "primitive" inoculant.

Compositions in liquid form comprise on average at least 106 CFU per mL. These inoculants are typically formulated as a bacterial suspension in a solution containing water and/or mineral oils and/or organic oils.

The composition can also be in solid form such as powder or granules. According to this formulation, the bacteria may be encapsulated in polymeric matrices such as alginate beads/granules. Typically, the bacteria are formulated in a carrier consisting of inert materials (such as alginate) and the mixture is made into a granular or powder form. The formulation can then be freeze-dried. Typically, freeze-drying can be performed in the presence of a cryoprotectant such as sucrose (for example present in an amount between 0 and 10%, specifically 5% by weight).

The bacterial strain or composition in accordance with the present invention can be used in a soil fertilization process. Thus, in another aspect, the present invention relates to a fertilization process, said process comprising a step in which the composition or the bacterial strain in accordance with the invention is applied to a plant or to growing medium such as soil.

A "fertilization process" aims at providing a growing medium with the mineral elements necessary for the development of a plant. The growing medium can be the soil, but also a growing support (for all market gardening applications, whether soilless or not) such as potting soils, but also supports for aquaponics, hydroponics or aeroponics. Therefore, "fertilization", as used herein, means both the fertilization of crops and the amendment of uncultivated soil.

In the context of the present invention the soil can be any type of soil according to the international soil classification system (FAO-World Reference Base).

The "plant" can be any living being belonging to the plant kingdom, whether cultivated or not. The plant is a terrestrial plant. It can be a woody plant or an herbaceous plant. The plant can, for example, be selected from the Poaceae, leguminous plants (Fabaceae) or oil-seed plants.

In a particular embodiment, the plant is a cereal selected from the group consisting of maize (*Zea mays* L.), rice (*Oryza sativa, Oryza* glaberrina), the various species of wheat (*Triticum aestivum; Triticum spelta; Triticum durum; Triticum dicoccum; Triticum turgidum* L. subsp. *turanicum; Triticum monococcum*), barley (*Hordeum vulgare* L. subsp. *vulgare; hordeum hexastichum*); sorghum (*Sorghum bicolor*); oats (*Avena sativa*), millet (*Pennisetum glaucum;*

*Panicum milliaceum; Setaria italica; Panicum sumatrense*), rye (*Secale cereale*), triticale (Triticosecale).

The "plants" are typically crops:
- field crop plants are typically selected from peanuts, spring and winter oats, fodder and industrial beets, soft winter and spring wheat, durum wheat, bromegrass, orchard grass, spelt, fescue, timothy, grain, forage and silage maize, millet, *miscanthus*, moha forage and grain, spring and winter barley, panic grass, English and Italian ryegrass, rice, spring and winter rye, sorghum, switchgrass, spring and winter triticale, spring and winter camelina, hemp, winter and spring rapeseed, canola, spring and winter white and brown mustard, turnip rape, pastel, spring and winter fava bean, bird's-foot trefoil, lupin, alfalfa, spring and winter peas, forage and protein peas, sainfoin, soybeans, white, red and red clover, vetch, hops, buckwheat, spring and winter flax (oilseed and textile), tobacco and sunflower;
- plants grown in fallow are typically selected from English and Italian ryegrass, Persian clover, white mustard, phacelia, white, red or purple clover and vetch;
- vegetable crops are typically selected from garlic, dill, artichoke, asparagus, eggplant, beet, broccoli, cardoon, carrot, celery root and stalk, tuberous chervil, chicory, Chinese cabbage, Brussels sprouts, leafy cabbage, head cabbage, cauliflower, kohlrabi, watercress, cucumber, gherkins, zucchini, melon, watermelon, pumpkin, shallot, spinach, fennel, fava bean, flageolet, strawberry, beans, lettuce, dry and fresh lentils, maize, turnip, cowpea, onion, parsley, chili, leek, peas, bell pepper, potato, purslane, radish, horseradish, rhubarb, arugula, rutabaga, salsify, curly endive, black salsify, tomato and Jerusalem artichoke;
- fruit crops such as lemon, clementine, lime, mandarin, orange, grapefruit, quince, fig, almond, chestnut, hazelnut, walnut, apricot, cherry, jujube, cherry-plum, nectarine, peach, plum, kiwi, nashi, medlar, olive, cranberry, black currant, rose hip, raspberry and other *Rubus*, currant, blackberry, blueberry, black elder, pear and apple;
- seed-bearing crops are typically selected from beet, brome, cocksfoot, fescue, ryegrass, seed-bearing forage legumes, seed-bearing umbellifers, seed fennel, seed bean, seed lupin, seed trefoil, seed alfalfa, seed maize, hemp, flax, *chrysanthemum*, bitter apple, wallflower, carnation, pansy, sweet pea, queen daisy, hollyhock, beet, carrot, celery, annual and biennial chicory, cabbage, chives, cucurbits, shallot, spinach, beans, lettuce, lamb's lettuce, turnips, onions, parsnips, parsley, leeks, peas, chickpeas, radishes, arugula, dill, chervil, coriander and clover;
- plants cultivated in ornamental crops are typically selected from conifers, broad-leaved trees, elms, lilies, *Hippeastrum, narcissus*, nerine, iris, hyacinth, lily, lily of the valley, gladiola, *hydrangea*, carnation, pale iris, palm, *pelargonium*, roses, tulips and other floral species;
- plants cultivated in tropical crops are typically pineapple and other anacardiaceous, avocado, banana, sugar cane, passion fruit, Chinese cabbage, cassava, sweet potato, yam, mango and *papaya*;
- plants grown for viticulture such as wine or table grapes (including the various species of vines); and
- plants cultivated for aromatic, perfume or medicinal purposes are typically selected from wormwood, yarrow, mugwort, costmary, burdock, dill, Roman chamomile, spices, *angelica*, basil, caraway, chervil, chives tarragon, bay leaves, rosemary, mint, parsley, sage, gentian, lavender and lavandin, lovage, evening primrose, oregano, borage, poppy seed, safflower, goosefoot, squash, castor oil, sesame, savory, marigold and thyme.

The "plant" in accordance with the invention may be selected from any of the crop species listed above, and particularly from the different varieties of these species.

Preferably, the "plants" in accordance with the invention are field crops, vegetable crops (including soilless) and viticulture, as defined above.

The application can be performed at any stage of plant development. The application can for example be performed directly on the seeds (for example by coating just before sowing or with precoated seeds with mixtures of carboxymethyl cellulose and starch as a coating base), on the soils to be cultivated or on the liquid or solid culture carriers (before or after sowing), for example by distribution of the inoculum in the seed line (for example by mixing the inoculum with clay microgranules distributed in the seed line or by direct inoculation on seeds using adhesive liquids), directly on the plant by foliar spraying or directly on a plant explant or on a cutting.

Typically, when applied directly to the seed, the composition is mixed with the seed by hand, in a rotary drum, or in a mixer. This mixing may require the addition of adhesives, such as gum arabic, carboxymethyl cellulose, sucrose solution or vegetable oils, to ensure that the seeds are covered with the necessary number of bacteria (see for example Senoo K, Narumi I, 2006. Carrier materials. p. 41-49; BiofertilizerManual. Japan Atomic Industrial Forum (JAIF)). After this mixing, the seeds are usually dried. Alternatively, the composition can be sprayed onto the seeds. The sprayed seeds are then sown after drying.

Typically, when the composition is applied directly to the soil to be cultivated, it is in granular form and distributed in the seed line. Alternatively, when in liquid form, the composition can be sprayed onto the soil to be cultivated.

Alternatively, when the growing medium is a support for soilless culture, such as aeroponics, hydroponics, or aquaponics, the composition can be directly mixed with the culture substrate, for example in the form of peat.

Typically, the application will be done at sowing time (by application on the soil or by seed coating) or by inoculation of the culture substrates for soilless crops.

According to another embodiment, the present invention also relates to the use of the bacterial strain deposited on Oct. 24, 2018, at the Collection Nationale de Culture de Microorganismes (CNCM), 28 rue du Dr. Roux, 75724 PARIS CEDEX 15, under the Budapest Treaty under number CNCM I-5373 as biofertilizer.

The invention also relates to the use of the bacterial strain deposited on Oct. 24, 2018, at the Collection Nationale de Culture de Microorganismes (CNCM), 28 rue du Dr. Roux, 75724 PARIS CEDEX 15, under the Budapest Treaty under number CNCM I-5373 as phytostimulant.

The following examples illustrate the invention in greater detail but should not be construed as limiting its scope.

BRIEF DESCRIPTION OF THE DRAWINGS

FIG. 1 represents the protease activity of the soil after inoculation with the strain in accordance with the invention;

FIG. 2 represents the nitrate content in the soil after inoculation with the strain in accordance with the invention;

EXAMPLES

Example 1: Analysis of the Biofertilizer Properties of the Strain of Interest on Soil Microcosm (Controlled Conditions)

Materials and methods: A "model" soil was taken from an agricultural plot at the ENSAIA experimental farm. The soil (silty clay; OM 4.5%; total N 0.3%; C/N 13.8; $pH_{water}$ 6.5) was sieved to 5 mm and then stored at room temperature until use. Soil microcosms were made by placing 70 g of soil at 60% of its water holding capacity in 0.5 L Le Parfait jars. The microcosms were pre-incubated for 2 weeks at 20° C. and then inoculated with 5 mL of $7*10^9$ CFU bacterial suspension (i.e., $10^8$ CFU/g fresh soil) of the selected bacterial strain. Control microcosms were treated with 5 mL of sterile saline. The soil microcosms, at 80% water holding capacity, were then incubated at 20° C. in the dark. Soil samples were taken at 0, 3, 7, 14 and 28 days after inoculation. Four replicates per treatment and sampling time were performed. At each sampling time, a set of variables were measured within 48 h after sampling, namely (i) soil microbial enzymatic activities in relation to N, S and P dynamics, (ii) measurements of water-soluble C and N contents, (iii) microbial C and N biomass, (iv) mineral N, S and P contents and (v) soil amino acid contents. Soil samples were immediately frozen at −20° C. for DNA extractions and 16S rDNA gene abundance measurements.

Potential arylsulfatase activity in the soil was measured according to the protocol of Tabatabai and Bremner (1970). Protease potential activity was measured according to the protocol of Ladd and Butler (1972). Potential phosphatase activity was measured according to the protocol of Dick et al. (1996). Finally, potential leucine-aminopeptidase activity was measured according to the protocol of Spungin and Blumberg (1989).

To estimate the soluble organic N and mineral N contents of the soils, 10 g of fresh soil was extracted with 50 mL of 1 M KCL for 45 min using a revolution mixer. Extracts were filtered through Whatman No. 42 filter (Harper, 1924) and stored at −20° C. until analysis. The mineral N contents ($NO_3^-$ and $NH_4^+$) of the extracts were determined using a SAN++ CFA molecular absorption spectrophotometer (Skalar Analytical, Breda, The Netherlands) by the INRA, Nancy, analysis unit. Amino acids were quantified according to the protocol of Darrouzet-Nardi et al. (2013). Soluble C and N were extracted with hot water as described by Vong et al. (2007). The C and N content of the hot water extracts was determined with a TOC-V CHS (Shimadzu, Kyoto, Japan).

$SO_4^{2-}$ were extracted from the soil by revolution mixing of 10 g of soil in 50 mL of 16 mM $KH_2PO_4$ for 45 min (Walker and Doornenbal, 1972) and then filtered a first time on Whatman No. 42 paper and a second time on a 0.45 μm pore size filter. $SO_4^{2-}$ from the $KH_2PO_4$ extracts were subsequently determined by ion chromatography (Dionex).

$PO_4^{2-}$ were extracted by revolution mixing of 5 g of soil in 50 mL of 0.5 M $NaHCO_3$ for 45 min and then filtered through Whatman No. 42 paper following the protocol of Hedley et al. (1982). $PO_4^{2-}$ from the $NaHCO_3$ extracts were subsequently determined according to the protocol of Irving and McLaughlin (1990).

Microbial C and N biomasses were measured by the fumigation-extraction method (Vance et al., 1987). C and N concentrations of fumigated and unfumigated 0.5 M $K_2SO_4$ extracts filtered on Whatman No. 42 were determined with a TOC-V CHS (Shimadzu, Kyoto, Japan). Microbial biomasses were determined by difference between fumigated and unfumigated extracts and division by an extraction coefficient of 0.45 for microbial C biomass (Vance et al., 1987) and 0.54 for microbial N biomass (Brookes et al., 1985).

Results: Under controlled conditions, the *Microbacterium*-affiliated strain (M) stimulates certain soil microbial activities involved in the mineralization of organic matter, without changing the size of the soil microbial biomass. Thus, microbial activities related to N decomposition are significantly higher in inoculated soils compared with uninoculated soils. Over 28 days of incubation, protease activity, which is involved in the breakdown of protein, the main form of organic N in soils, was on average 50% higher in soils inoculated with the M strain compared with uninoculated soils (FIG. 1). Leucine aminopeptidase activity, which degrades peptides released by proteases into amino acids, was increased by 3% to 23% in soils inoculated with the M strain from 14 days after inoculation. Arylsulfatase activities that mineralize sulfate esters, a major and among the most labile form of organic S in soils, are also stimulated in inoculated soils, weakly 3 days after inoculation (+9% activity in soils inoculated with the M strain) and strongly 14 days after inoculation (+109% activity in soils inoculated with the M strain).

The M strain improves the availability of mineral N in the form of soil nitrate (FIG. 2), which is the main source of N for plant nutrition.

Example 2: Analysis of the Phytostimulant Properties of the Strains of Interest (Controlled Conditions)

Materials and methods: A first experiment under gnotobiotic conditions was set up to study the effect of the bacterial M strain on the growth and root architecture of maize seedlings (Pioneer Hi Bred). The seeds used were surface sterilized. To this end, the seeds were successively placed in the presence of 70% ethanol for 5 min and 5% sodium hypochlorite for 10 min. The seeds were then rinsed 5 times with sterile distilled water. 100 μL of the last rinse water was spread on NB agar medium to verify the efficiency of the surface sterilization.

Roughly 25 sterilized seeds were then germinated in 13.5 cm diameter Petri dishes on sterile Whatman No. 3 filter paper moistened with 10 mL sterile distilled water. The Petri dishes were placed in the dark for 3 days at 28° C. Four pre-germinated seeds were then selected and arranged in an equatorial line in a 13.5 cm diameter Petri dish. Each seed was inoculated with 100 μL of bacterial suspension (109 bacteria/seed) of the selected strain. The bacterial inoculum was prepared from a culture at 109 CFU/mL. One mL of culture was centrifuged at 10 000 rpm for 10 min and then the pellet was taken up in 100 μL of sterile saline. Control pre-germinated seeds received 100 μL of sterile saline. In total, 4 replicates were performed per treatment. The Petri dishes were placed in a climatic chamber with a photoperiod of 16 h, a temperature of 23° C. day and 18° C. night for 6 days. After incubation, root parts were collected. A set of root traits were analyzed. To this end, the root system was spread in a thin layer of water, in a Plexiglas tank (1.5*20*30 cm), using fine tweezers. The root system was then scanned (Expression 1640XL scanner, Epson) and the images obtained were analyzed with WinRhizo® software (Régent Instruments Inc., Quebec, Canada). The total length (cm), the length of fine (diameter<2 mm) and coarse (diameter>2 mm) roots, the total surface area ($cm^2$), the surface area of fine and coarse roots and the average diameter (mm) of the roots were estimated. After analysis, the roots were gently dried on filter paper and weighed to estimate the fresh mass. They were then placed in an oven at 80° C. for 48 h to determine the dry mass.

A second experiment aimed at evaluating the effect of the M strain on the growth, physiology and nutritional status of maize during the early stages of development, as well as on the biological functioning and the content of mineral elements in the maize rhizosphere. The soil (silty clay; OM 1.6%; total N 0.12%; C/N 7.8; $pH_{water}$ 7.5) was collected from an agricultural plot (Saint Martin des Champs, 77), air-dried and sieved to 5 mm. Before use, the soil was mixed with 10% (m/m) aquarium sand to facilitate subsequent root collection.

The inoculation of maize with the bacterial strain of interest was performed at sowing time, on sterilized and germinated seeds with 1 mL of an inoculum at a concentration of $10^8$ CFU/mL. Sterilized, germinated but uninoculated seeds were used as a control. One seed was placed at a depth of about 2 cm in a PVC tube (5*20 cm) containing 330 g of soil-sand mixture. This substrate was maintained at 80% of its water holding capacity by weighing the tubes 5 times a week and watering, if necessary. At the 1-2 leaf, 3-4 leaf, 5 leaf and 5-6 leaf stages, 4 tubes of each treatment modality were randomly selected and opened with a circular saw. After opening the tubes, the aerial parts were separated from the soil-root system and collected. The roots were separated from the soil, collected with tweezers and then washed with tap water. The aerial and root parts of the plants and the soil were stored at 4° C. until all variables were analyzed. An aliquot of soil was frozen at −20° C. for subsequent molecular analyses.

At the plant level, fresh mass and dry mass of aerial and root parts were measured. Root architecture was also analyzed as previously described (experiment under gnotobiotic conditions). At the level of maize rhizosphere soil, the variables of microbial abundance, microbial enzymatic activities and mineral element content were measured as described in the context of the soil microcosm experiment.
Results:

In the second experiment, we analyzed the effect of the M strain on the growth and nutritional status of maize grown under controlled conditions up to the 6-leaf stage as well as the biological functioning and availability of mineral elements in the rhizosphere of this maize.

At the plant level, while the strain does not influence the biomass of the aerial parts of the maize or their height, it does alter root growth. Thus, the fresh root biomass of plants inoculated with the M strain is 20% higher (p-0,01) than that of control plants at the 3-4 leaf stage. The surface area of fine roots (diameter<2 mm) was greater for inoculated plants compared with the control. These results tend to confirm the results obtained under gnotobiotic conditions.

Concerning the effects of M strain inoculation on rhizosphere soil functioning, measurements of microbial abundance, microbial enzymatic activities involved in N, S and P dynamics and mineral element contents were performed. The main effects of M strain inoculation on soil enzyme activities related to N, S and P cycles were observed at the maize 3-4 leaf stage. Arylsulfatase activity involved in S mineralization was significantly increased in the rhizosphere of plants inoculated with the M strain (+89%) compared with the control at the 3-4 leaf stage. At the 5-6 leaf stage, this activity remained higher in inoculated soils (+18% for the M strain).

Example 3: Use of Molecular Markers to Discriminate the M Strain

The possibility of discriminating bacterial strains with RAPD-type markers was validated by comparing the profile of the M strain with other strains, in particular from the genus *Pseudomonas* (which is highly abundant in natural environments).

The strains tested are listed in the table below:

TABLE 1

List of strains tested

| Strain code | Strain name |
| --- | --- |
| Achromo | *Achromobacter* sp. |
| Ps.chloro | *Pseudomonas chlororaphis* |
| Ps.sp | *Pseudomonas* sp. |
| Ps.putida | *Pseudomonas putida* |
| Enterob | *Enterobacter ludwigii* |
| Ps-1 | *Pseudomonas moraviensis* |
| Ps-2 | *Pseudomonas moraviensis* |
| Micro-1 | *Microbacterium resistens* (M strain) |
| Micro-2 | *Microbacterium resistens* (M strain) |

Two RAPD-type markers were tested: M13 5'-GAGGGTGGCGGTTCT-3' (SEQ ID NO: 1) and RAPD2 5'-AGCAGCGTGG-3' (SEQ ID NO:2). Amplification reactions were performed in a final volume of 12.5 μL in the presence of 15 ng DNA and 25 μM primers. Amplicons were separated on a 2% agarose gel to reveal the profiles.

Both markers are discriminating even against bacteria of the same genus. A better repeatability is observed for the M13 marker.

Example 4: Production of the M Strain

The scale-up was performed in an Applikon® bioreactor in a final volume of 4 L. The medium used was composed of 10 g/L whole milk powder and 5 g/L yeast extract. The tests will make it possible to determine the kLa (oxygen transfer coefficient), a parameter for scaling up (50 and then 500 L bioreactors). The optimal temperature is 30° C. (see table below).

TABLE 2

Conditions for producing the strain

| Parameter | Aeration | Stirring | pH | Temperature |
| --- | --- | --- | --- | --- |
| *M. resistens* M strain | 2 vvm | 150 rpm | 6.9-7.1 | 30° C. |

Tests conducted in 5 L fermenters produced microbial biomass of the M strain at an average of $1.11^{E+09}$ CFU/mL.

Example 5: Drying of the M Strain

The M strain shows very good survival to the freeze-drying process for the conditions with cryoprotectant, even more marked for the condition with sucrose. The freeze-drying schedules are presented in Table 3. In addition, freezing the samples for freeze-drying had no impact on the viability of the bacteria. The aw of the samples is at most about 0.150 and ensures good microbiological stability (viability and shelf life). The total duration of freeze-drying is 47 hours.

TABLE 3

Freeze-drying schedules

| Step | Final temperature of the shelves (° C.) | Ramp (min) | Pressure (µbar) | Step duration (min) |
|---|---|---|---|---|
| Freezing | −45 | Before loading | Atmo | 120 |
| Primary Drying | −30 | 60 | 50 | 990 |
|  | −10 | 150 | 50 | 1350 |
|  | 10 | 120 | 50 | 300 |
| Secondary Drying | 20 | 90 | 50 | 60 |

With cryoprotectant, the loss of viability is negligible. Thus, a positive effect of cryoprotectant (5% sucrose) is observed. Without cryoprotectant, the survival of the strain remains very acceptable at about half a log (Table 4).

TABLE 4

Strain viability

| Condition | Viability (CFU/mL) before freeze-drying | Viability before freeze-drying (logCFU/mL) | Viability after freeze-drying (CFU/mL) | Viability after freeze-drying (CFU/g DM) | Viability after freeze-drying (logCFU/mL) | Loss of viability (log reduction) |
|---|---|---|---|---|---|---|
| The M strain without cryoprotectant | 3.80E+10 | 10.58 | 1.03E+10 | 3.32E+11 | 10.01 | 0.57 |
| The M strain with 5% sucrose | 3.40E+10 | 10.53 | 2.48E+10 | 8.35E+11 | 10.39 | 0.14 |

---

---

The invention claimed is:

1. A fertilization process comprising a step in which the bacterial strain deposited on Oct. 24, 2018, at the Collection Nationale de Culture de Microorganismes (CNCM), 28 rue du Dr Roux, 75724 PARIS CEDEX 15, under the Budapest Treaty under number CNCM I-5373, or a composition comprising said bacterial strain, is applied to a plant or to a soil.

2. The fertilization process according to claim 1, wherein said plant is selected from field crop plants, vegetable crop plants and plants grown in viticulture.

3. The fertilization process according to claim 1, wherein the application is made at sowing time, by application to the soil or by coating the seeds.

4. The fertilization process according to claim 1, wherein the application is made by inoculation of growing substrates intended for soilless cultivation.

5. The fertilization process according to claim 1, wherein said composition is in powder, granule, cream or liquid form.

6. The fertilization process according to claim 1, wherein said composition is in liquid form.

7. The fertilization process according to claim 1, wherein said composition comprises the bacterial strain as a suspension in a solution containing water and/or mineral oils and/or organic oils.

8. A method for biofertilizing a soil, comprising a step of applying the bacterial strain deposited on Oct. 24, 2018, at the Collection Nationale de Culture de Microorganismes (CNCM), 28 rue du Dr Roux, 75724 PARIS CEDEX 15, under the Budapest Treaty under number CNCM I-5373 to a soil.

9. A method for stimulating a plant growth, comprising a step of applying the bacterial strain deposited on Oct. 24, 2018, at the Collection Nationale de Culture de Microorganismes (CNCM), 28 rue du Dr Roux, 75724 PARIS CEDEX 15, under the Budapest Treaty under number CNCM I-5373 to a plant.

* * * * *

```
SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: M13 primer

<400> SEQUENCE: 1
gagggtggcg gttct                                                      15

<210> SEQ ID NO 2
<211> LENGTH: 10
<212> TYPE: DNA
<213> ORGANISM: Artificial Sequence
<220> FEATURE:
<223> OTHER INFORMATION: RAPD2 primer

<400> SEQUENCE: 2
agcagcgtgg                                                            10
```